(12) United States Patent
Pujol et al.

(10) Patent No.: US 8,640,696 B2
(45) Date of Patent: Feb. 4, 2014

(54) SYSTEM AND METHOD FOR DETERMINING HUMIDITY IN A RESPIRATORY TREATMENT SYSTEM

(75) Inventors: J. Raymond Pujol, Murrysville, PA (US); William Perroz, Jr., Vandergrift, PA (US); Robert G. Rybicki, Pittsburgh, PA (US)

(73) Assignee: RIC Investments LLC, Wilmington, DE (US)

( * ) Notice: Subject to any disclaimer, the term of this patent is extended or adjusted under 35 U.S.C. 154(b) by 1597 days.

(21) Appl. No.: 11/481,323

(22) Filed: Jul. 5, 2006

(65) Prior Publication Data
US 2008/0308100 A1    Dec. 18, 2008

Related U.S. Application Data

(60) Provisional application No. 60/697,130, filed on Jul. 7, 2005.

(51) Int. Cl.
*A61M 16/16* (2006.01)
*A61M 16/00* (2006.01)

(52) U.S. Cl.
USPC ............. 128/203.26; 128/203.14; 128/204.18

(58) Field of Classification Search
USPC ............. 128/200.24, 203.17, 203.26, 203.27, 128/204.18, 204.21, 204.22, 128/200.11–200.13, 203.12, 203.14, 203.16
See application file for complete search history.

(56) References Cited

U.S. PATENT DOCUMENTS

| | | | |
|---|---|---|---|
| 3,659,604 A | 5/1972 | Melville et al. | |
| 4,038,980 A | 8/1977 | Fodor | |
| 4,367,734 A | 1/1983 | Benthin | |
| 5,031,612 A | 7/1991 | Clementi | |
| 5,092,326 A | 3/1992 | Winn et al. | |
| 5,163,423 A | 11/1992 | Suzuki | |
| 5,368,786 A | 11/1994 | Dinauer et al. | |
| 5,429,123 A | 7/1995 | Shaffer et al. | |
| 5,468,961 A | 11/1995 | Gradon et al. | |
| 5,558,084 A | 9/1996 | Daniell et al. | |
| 5,769,071 A | 6/1998 | Turnbull | |
| 5,988,164 A | 11/1999 | Paluch | |

(Continued)

FOREIGN PATENT DOCUMENTS

| | | |
|---|---|---|
| EP | 1 138 341 A2 | 10/2001 |
| JP | 2005537083 A | 12/2005 |
| WO | WO2004020031 A1 | 3/2004 |
| WO | WO2008024001 A1 | 2/2008 |

*Primary Examiner* — Justine Yu
*Assistant Examiner* — Valerie L Skorupa
(74) *Attorney, Agent, or Firm* — Michael W. Haas

(57) ABSTRACT

A patient treatment system and method comprising a patient circuit, a pressurizing flow module disposed in the patient circuit, a humidifier disposed in the patient circuit, a monitor, sensors within the patient circuit, and a processor. The patient circuit delivers a flow of gas from a gas source to an airway of a patient. The pressurizing flow module elevates the pressure of the gas within the patient circuit. The humidifier elevates the humidity of the gas in the patient circuit to a circuit humidity level. The monitor monitors at least one parameter of the gas from the gas source. The sensors generate corresponding signals that can be processed to estimate a rate at which vapor is added to the gas in the patient circuit. The processor determines the humidity level of the gas in the patient circuit downstream from the humidifier based on the signals generated by the sensors and the at least one parameter of the gas in the gas source.

18 Claims, 6 Drawing Sheets

(56) References Cited

U.S. PATENT DOCUMENTS

| | | | |
|---|---|---|---|
| 6,050,260 A * | 4/2000 | Daniell et al. | 128/204.22 |
| 6,095,505 A | 8/2000 | Miller | |
| 6,102,037 A * | 8/2000 | Koch | 128/203.26 |
| 6,272,933 B1 | 8/2001 | Gradon et al. | |
| 6,349,722 B1 | 2/2002 | Gradon et al. | |
| 6,349,724 B1 | 2/2002 | Burton et al. | |
| 6,367,472 B1 | 4/2002 | Koch | |
| 6,435,180 B1 | 8/2002 | Hewson et al. | |
| 2001/0050080 A1 * | 12/2001 | Seakins et al. | 128/203.16 |
| 2002/0017298 A1 | 2/2002 | Koch | |
| 2002/0050656 A1 | 5/2002 | Offier et al. | |
| 2002/0112725 A1 | 8/2002 | Thudor et al. | |
| 2002/0129815 A1 | 9/2002 | McPhee | |
| 2002/0139367 A1 | 10/2002 | McPhee | |
| 2004/0079370 A1 * | 4/2004 | Gradon et al. | 128/203.26 |
| 2004/0221844 A1 * | 11/2004 | Hunt et al. | 128/204.17 |
| 2007/0137646 A1 | 6/2007 | Weinstein | |

\* cited by examiner

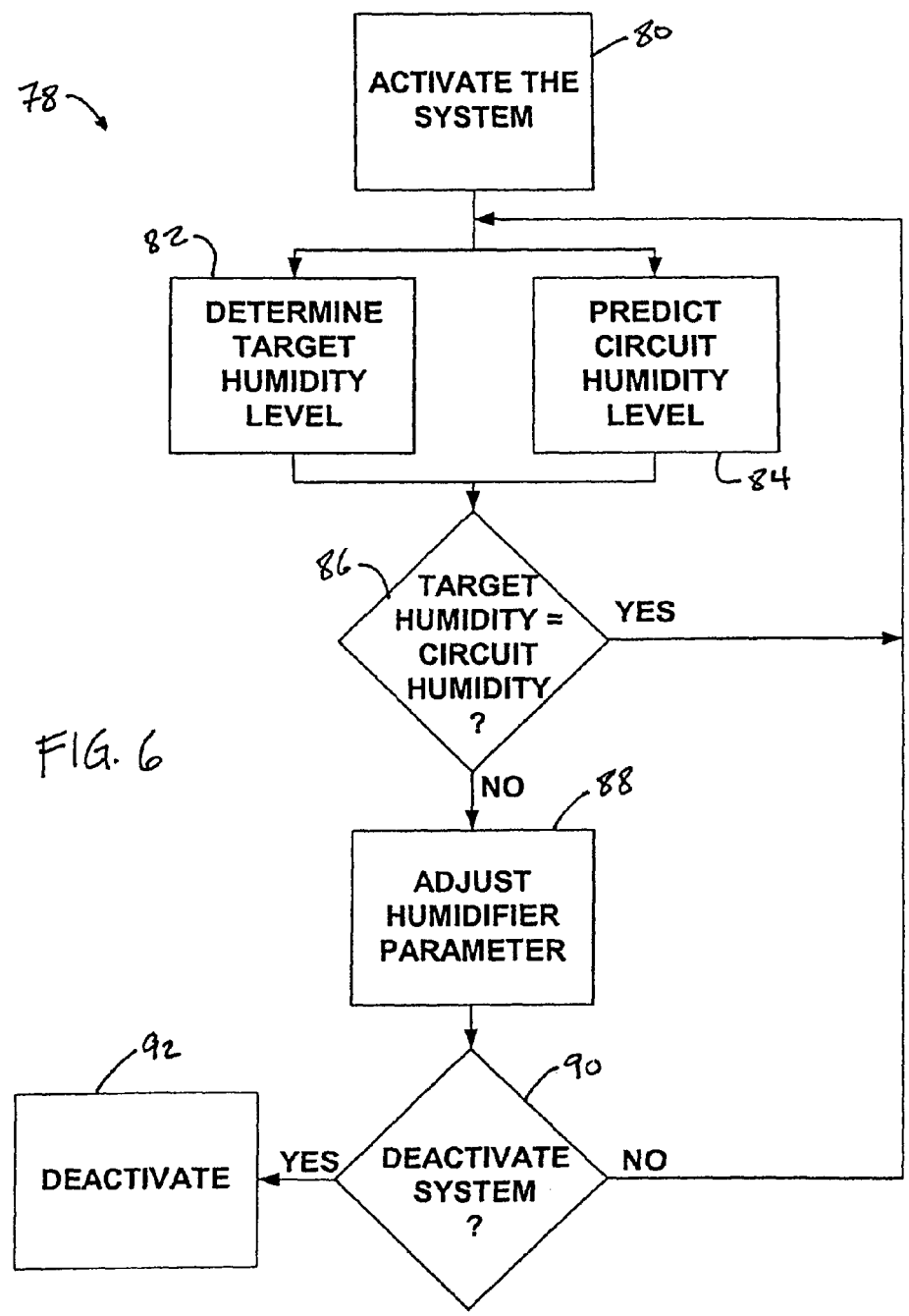

SYSTEM AND METHOD FOR DETERMINING HUMIDITY IN A RESPIRATORY TREATMENT SYSTEM

CROSS-REFERENCE TO RELATED APPLICATIONS

This application claims priority under 35 U.S.C. §119(e) from provisional U.S. patent application No. 60/697,130 filed Jul. 7, 2005 the contents of which are incorporated herein by reference.

BACKGROUND OF THE INVENTION

1. Field of the Invention

The invention relates to respiratory treatment systems, and, in particular, to a system and method of humidifying gas in a respiratory treatment system based on the ambient conditions.

2. Description of the Related Art

Humidifiers are commonly used with ventilators, pressure support systems, and other respiratory devices to add humidity to the gas being supplied to a patient via a patient circuit. The humidity added to the gas supplied to the patient by a conventional ventilator or pressure support system is typically monitored and/or controlled in a feedback loop to provide a consistent humidity level. Typically, the humidity has been monitored by placing a temperature and/or humidity sensor in the ventilator itself, or within the patient circuit to monitor the humidity of the air in the ventilator. An example of such a conventional feedback humidification system is described in published U.S. patent application Ser. No. 09/808,567 (pub. no. 2001/0050080).

Such systems, however, may not provide an appropriate level of humidity to the patient. One reason, discovered by the present inventors, is that conventional feedback humidification system do not take into consideration the condition of the ambient environment in which the patient and ventilator/pressure support system are located.

SUMMARY OF THE INVENTION

Accordingly, it is an object of the present invention to provide a method for determining humidity of gas delivered to a user that overcomes the shortcomings of conventional humidification sensing methods and apparatus. This object is achieved according to one embodiment of the present invention by providing a method of determining humidity of gas delivered to a user. The method of the present invention includes determining a humidity level of ambient gas outside a patient circuit, which is used to deliver the flow of gas to the user's airway. Gas is drawn into the patient circuit, and vapor is added to the gas drawn into the circuit. The humidity level of the gas drawn into the patient circuit is determined based upon the humidity of ambient gas outside the circuit and a rate at which the vapor is added to the gas drawn into the circuit.

Another aspect of the invention relates to a patient treatment system that includes a patient circuit, a pressurizing flow module disposed in the patient circuit, a humidifier disposed in the gas circuit, a monitor, sensors within the circuit, and a processor. The patient circuit delivers a flow of gas from a gas source to an airway of a patient. The pressurizing flow module elevates the pressure of the gas within the patient circuit, is the pressure from the gas source is below the therapeutic level, or controls the pressure of the flow of gas delivered to the user if the pressure from the gas source is at or above the therapeutic level. The humidifier elevates the humidity of the gas in the patient circuit to a circuit humidity level. The monitor monitors at least one parameter of the gas from the gas source. The sensors generate corresponding signals that can be processed to estimate a rate at which vapor is added to the gas in the circuit. The processor determines the humidity level of the gas in the circuit downstream from the humidifier based on the signals generated by the sensors and the at least one parameter of the gas in the gas source.

Another aspect of the present invention relates to a method for determining humidity of gas within a patient circuit. The method according to this aspect of the present invention comprises determining a humidity of ambient gas outside the patient circuit, drawing ambient gas into the patient circuit, pressurizing the gas within the patient circuit, adding humidity to the gas within the patient circuit, and determining a humidity level of the gas within the patient circuit after the humidity has been added thereto. Determining the humidity level of the gas in the patient circuit is accomplished based upon the humidity of ambient gas outside the circuit, and at least one parameter of the gas (other than humidity within the circuit).

Another aspect of the invention relates to a method of delivering gas from a gas source to a patient along a patient circuit. The pressure of the gas within the patient circuit is elevated by a pressurizing flow module, and the humidity level of the gas within the patient circuit is elevated by a humidifier. In one embodiment, the method comprises determining the pressure of the gas within the patient circuit, determining a flow rate of the gas within the patient circuit, determining at least one parameter of the gas in the gas source, determining at least one parameter of the operation of the humidifier, and determining a humidity level of the gas in the patient circuit downstream from the humidifier based at least in part on the flow rate of the gas within the patient circuit, the pressure of the gas within the patient circuit, the at least one parameter of the gas in the gas source, and the at least one parameter of the operation of the humidifier.

Another aspect of the invention relates to a method of delivering gas from a gas source to a patient along a patient circuit, wherein the pressure of the gas within the patient circuit is elevated by a pressurizing flow module, and the humidity level of the gas within the circuit is elevated by a humidifier. The method comprises determining the pressure of the gas within the patient circuit, determining a flow rate of the gas within the patient circuit, determining a humidity level of the gas in the gas source, determining a temperature associated with the humidifier, and determining a humidity level of the gas in the patient circuit downstream from the humidifier based at least in part on the flow rate of the gas within the patient circuit, the pressure of the gas within the patient circuit, the humidity level of the gas in the gas source, and the temperature associated with the humidifier.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise

BRIEF DESCRIPTION OF THE DRAWINGS

FIG. 6 illustrates a method of operating the patient treatment system, in accordance with an embodiment of the invention.

DETAILED DESCRIPTION OF THE EXEMPLARY EMBODIMENTS

Figure 1:
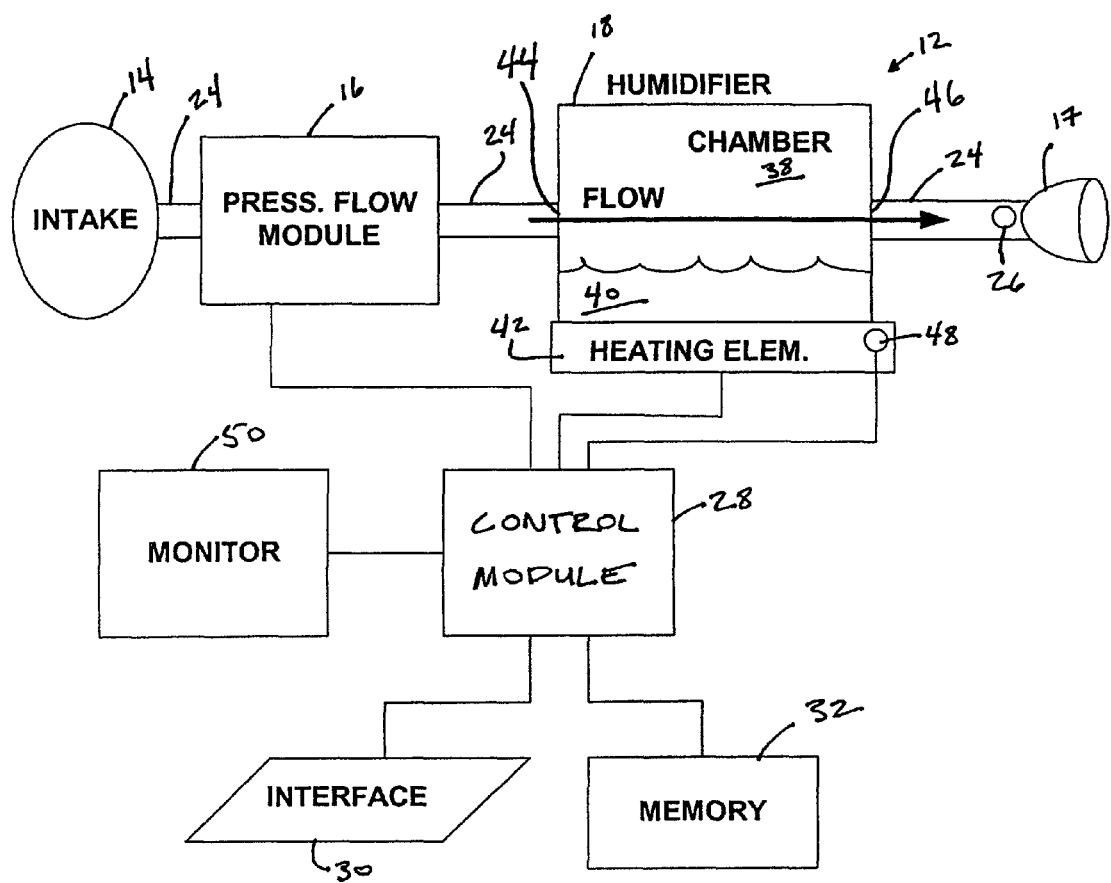
FIG. 1 illustrates a patient treatment system, including a humidifier, according to an embodiment of the invention.

FIG. 1 schematically illustrates an exemplary embodiment of a patient treatment system 10 according to the principles of the present invention. Patient treatment system 10 is capable of providing breathable gas to a patient while automatically controlling the pressure of the breathable gas according to a predetermined mode of ventilation. Patient treatment system 10 includes a patient circuit 12 that provides the breathable gas to the patient from a gas source.

In one embodiment, the gas source is ambient air, but may be other types of sources, as will be described later. The breathable gas is introduced into circuit 12 from the gas source at an intake 14. Intake 14 may include a port, a vent, or an opening. In some embodiments, intake 14 may include a filter that filters the breathable gas as it is introduced into circuit 12. As shown in FIG. 1, a pressurizing flow module 16 controls the pressure and flow of the gas in circuit 12 from intake 14 to a patient interface 17 where the breathable gas is delivered to an airway of the patient. Circuit 12 also includes a humidifier 18 that operates to elevate the humidity of the gas in circuit 12 to a selectably controllable circuit humidity level.

As also shown in FIG. 1, the patient treatment system 10 further includes a control module 28 that interfaces with a control interface 30, memory 32, and monitor 50, as will be described in detail later.

Figure 2:
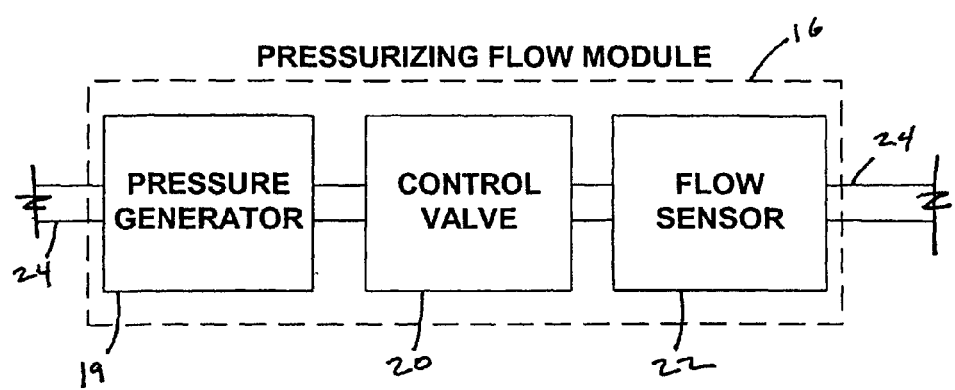
FIG. 2 illustrates an exemplary embodiment of a pressurizing flow module according to an embodiment of the invention.

Referring to FIG. 2, pressurizing flow module 16 is illustrated according to one exemplary embodiment of the invention. In the embodiment illustrated in FIG. 2, pressurizing flow module 16 includes a pressure generator 19 that receives the breathable gas in patient circuit 12 and elevates the pressure of that gas for delivery to the airway of a patient. Pressure generator 19 is any device, such as a pump, blower, piston, or bellows, that is capable of elevating the pressure of the received breathable gas for delivery to a patient. As mentioned above, the present invention also contemplates that gas other than ambient atmospheric air may be introduced into circuit 12 for delivery to the patient. In such embodiments, a pressurized canister or tank of gas containing air, oxygen, or other breathable gas mixture can supply the intake 14 to pressure generator 19. In another embodiment, pressure generator 19 need not be provided, but instead the breathable gas can by pressurized by the pressure of the canister or tank of pressurized gas itself, with the pressure delivered to the patient being controlled by a pressure regulator. In one embodiment, pressure generator 19 is a blower that is driven at a substantially constant speed during the course of the pressure support treatment to provide the gas in circuit 12 with a substantially constant elevated pressure and/or flow rate.

As illustrated in FIG. 2, the breathable gas in pressurizing flow module 16 is directed from pressure generator 19 to a control valve 20. As is described below, control valve 20, either alone or in combination with pressure generator 19, controls the circuit pressure and/or the circuit flow rate of the gas in circuit 12 downstream from pressurizing flow module 16. Examples of control valve 20 include at least one valve, such as sleeve or poppet valve, that exhausts gas from circuit 12 as a method of controlling the circuit pressure and circuit flow rate in circuit 12. U.S. Pat. No. 5,694,923, the contents of which are incorporated herein by reference, teaches a dual poppet valve system suitable for use as control valve 20 that exhausts gas to atmosphere and restricts the flow of gas from pressure generator 19 to the patient suitable for use as the control valve. In addition, U.S. Pat. No. 6,615,831, the contents of which are incorporated herein by reference, teaches a sleeve valve suitable for use as the control valve of the present invention.

Figure 3:
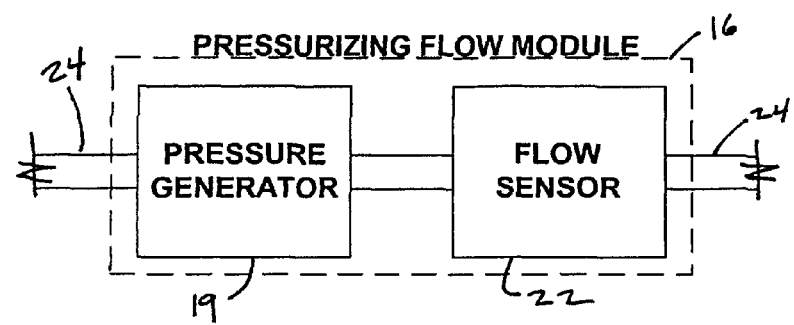
FIG. 3 illustrates an alternative exemplary configuration of the pressurizing flow module in accordance with an embodiment of the invention.

For embodiments wherein pressure generator 19 is a blower that operates at only one speed, then one or more control settings of control valve 20, such as the position of the valve element, can be adjusted to provide control over the circuit pressure and the circuit flow rate for the breathable gas in circuit 12. However, the present invention also contemplates embodiments in which one or more control settings related to the operation of pressure generator 19, such as a blower speed, are adjusted alone or in combination with the control settings of control valve 20 to control the circuit pressure and the circuit flow rate for the breathable gas delivered to the patient along circuit 12. For example, a circuit pressure and a circuit flow rate close to the desired circuit pressure and circuit flow rate can be set by adjusting an appropriate operating speed for pressure generator 19 (macro control). Fine tuning (micro control) of the circuit pressure and the circuit flow rate can then be provided by adjusting one or more control settings associated with control valve 20 so that the two, operating together, determine the final circuit pressure for the breathable gas in circuit 12 downstream from pressurizing flow module 16. If the operation of the pressure generator alone is used to control the pressure or the flow of gas in the patient circuit, control valve 20 can be omitted, as shown in FIG. 3.

Referring again to FIG. 2, pressurizing flow module 16 includes a pressure/flow sensor 22. Pressure/flow sensor 22 is a device, assembly, system, or combination thereof that is capable of outputting a signal indicative of a pressure, a flow, or both, associated with the gas in the patient circuit. In an exemplary embodiment, the pressure of the gas in patient circuit 12 is monitored using a conventional pressure sensor.

As a flow sensor, the flow of breathable gas output from control valve 20 is delivered to pressure/flow sensor 22, which outputs a signal indicative of the rate of flow of gas in conduit 24. This signal can be used to determine the instantaneous volume (V) of gas delivered to the patient, the instantaneous flow rate (V') of such gas to the patient, or both. Pressure/flow sensor 22 is any device suitable for measuring these parameters, such as a spirometer, pneumotach, variable orifice transducer, differential pressure transducer, or other conventional flow transducer.

In the illustrated embodiment, pressure/flow sensor 22 is provided within pressurizing flow module 16, at a location relatively distant from patient interface 17. The present invention, however, contemplates locating pressure/flow sensor 22 at any location along circuit 12 as well as at patient interface 17. For example, U.S. Pat. No. 6,017,315, the contents of which are incorporated herein by reference, teaches a quantitative flow member that is located at patient interface 17.

As noted above, the present invention contemplates that the pressure/flow sensor is any device capable of measure a parameter indicative of the flow of gas in the patient circuit. It is to be understood that gas flow can be determined by monitoring the operation of pressure generator 19, such as the voltage, current, or power provided to the blower, its operating speed, etc., all of which vary with the pressure or flow in the patient circuit. The present invention also contemplates monitoring the operation of control valve 20, such as the position of the valve, as a means for determining the flow of gas in the patient circuit, for it is known that the position of the valve in a feedback controlled pressure generating module corresponds to the flow of gas in the patient circuit. Thus, pressure/flow sensor 22 can be incorporated into pressure generator 19, control valve 20, or both.

An alternate embodiment of a pressurizing flow module 16' is illustrated in FIG. 3. Unlike in FIG. 2, where the circuit pressure and circuit flow rate are controlled by control valve 20, either alone or in combination with pressure generator 19, the embodiment of FIG. 3 controls the pressure of breathable gas delivered to the patient based solely on the output of pressure generator 19. For example, the control module 28 may control the pressure of breathable gas delivered to the patient by controlling only a motor speed of a blower associated with pressure generator 19. The embodiments of the present invention contemplate providing, if desired, ancillary feedback systems, such as a pressure monitor in circuit 12, motor speed monitor, valve monitor, or pressure generator output monitor that provides feedback data to the control module 28 for controlling the operation of pressurizing flow module 16.

Returning to the patient treatment system 10 illustrated in FIG. 1, the flow of breathable gas is carried between the various components in circuit 12 via sections of a conduit 24. In one embodiment, some or all of the various sections of conduit 24 may be provided by flexible tubing, rigid tubing, or by other members that would provide a conduit for the breathable gas therethrough. Thus, conduit 24 forms all or part of the patient circuit that communicates gas with the airway of the patient.

Patient interface 17 is any appliance, either invasive or non-invasive, such as a nasal mask, nasal/oral mask, total face mask, nasal cannula, endotracheal tube, or tracheal tube, suitable for communicating a supply of breathable gas to the airway of a patient. Patient interface assembly 17 may include headgear for mounting the appliance on the head of a patient. In the illustrated embodiment, patient interface 17 and/or conduit 24 includes a suitable exhaust port 26 for exhausting gas from these components to ambient atmosphere. Exhaust port 26 is preferably a passive exhaust port in the form of a continuously open port that imposes a flow restriction on the exhaust gas to permit control of the pressure of gas within patient interface 17. It is to be understood, however, that exhaust port 26 can be an active exhaust port that assumes different configurations to control the exhaust rate. Examples of suitable exhaust ports are taught, for example, in U.S. Pat. Nos. 5,725,296 and 5,937,855, the contents of which are incorporated herein by reference.

Control module 28 is operatively linked to pressurizing flow module 16 and humidifier 18. For example, in the embodiment of FIGS. 2 and 3, the output of sensor 22 is provided to control module 28, which comprises a processor and suitable programming for determining the instantaneous volume (V) of gas delivered to the patient, or the instantaneous flow rate (V') of such gas to the patient, or both based on the signals from sensor 22. For example, the instantaneous volume can be determined by integrating the measured flow rate. Because the flow sensor 22 is located relatively far from patient interface 17, in order to determine the actual flow rate of gas to the patient or the actuation flow rate of gas from the patient, which is considered a negative flow, control module 28 receives the output from sensor 22 as an estimated flow. Control module 28 processes this estimated flow information, for example, by performing leak estimation, to determine the actual flow at the patient's airway, as is known to those skilled in the art.

As can be appreciated from FIG. 1, control interface 30 provides data and commands to control module 28 and outputs, in human perceivable form, any information of interest. For example, commands may be provided at control interface 30 to control module 28 to adjust one or more control settings associated with patient treatment system 10. Control interface 30 is any device suitable to provide information and/or commands to control module 28 via an operative link and to present information to the patient, or another user, in a human perceivable format. Examples of a suitable input/output device includes a keypad, keyboard, touch pad, mouse, visual display (e.g., LCD or LED screen), microphone, speaker, switches, button, dials, lamps, or any other devices that allow a user to input information to and receive information from treatment system 10. Interface 30 can also include hardwired or wireless techniques for communicating information and/or commands with processor 40, such as a serial port, parallel port, USB port, RS-232 port, smart card terminal, modem port, etc.

In the embodiment illustrated in FIG. 1, patient circuit 12 is a single-limb circuit. It is to be understood, however, that the present invention also contemplates that patient circuit 12 can be a two-limb circuit, which is common in conventional ventilators. The first limb in a two-limb circuit, like patient circuit 12 shown in the figures except that it lacks an exhaust port, carries a flow of gas from a source of such gas to the patient. The second limb in a two-limb circuit carries the exhaust gases from the patient to ambient atmosphere. Typically, an active exhaust port or exhaust valve is provided in the second limb under the control of control module 28 to maintain a desired level of positive end expiratory pressure (PEEP) in the patient. In addition, patient circuit 12 and related components can include other conventional devices, such as a heater, bacteria filter, temperature sensor, pressure sensor, and a gas sensor (e.g., a capnometer that measures, monitors, analyzes, etc. the flow of gas to or from the patient).

Control module 28 controls the actuation of a control valve associated with pressurizing flow module 16 (e.g., control valve 20 of FIG. 2) by adjusting one or more control settings, thereby controlling the circuit pressure, the circuit flow rate, or both of the breathable gas in circuit 12. In accordance with the principles of the present invention, the pressure of the breathable gas is provided to the patient according to the CPAP, Bi-level, auto-titrating, PAV, C-Flex, Bi-Flex, or PPAP modes of ventilation or pressure support. Thus, control module 28 is suitably programmed with the necessary algorithm or algorithms for calculating the circuit pressure and circuit flow rate to be applied to the patient according to these modes of ventilation. Memory 32 is optionally provided and can be linked with control module 28 to provide storage for the algorithms or programs provided above, as well as other data associated with system 10.

As is shown in FIG. 1, humidifier 18 includes a chamber 38 that holds a reservoir of fluid 40. The fluid may be composed primarily, or entirely, of water. The reservoir of fluid 40 is heated by a heating element 42 to cause the reservoir of fluid 40 to evaporate, thereby producing vapor within chamber 38. As the gas in patient circuit 12 passes through chamber 38 from a chamber inlet 44 to a chamber outlet 46, the vapor in chamber 38 is delivered to the gas, thereby elevating the humidity of the gas in patient circuit 12 downstream from humidifier 18.

The amount by which the humidity level of the gas is increased by humidifier 18 depends on the amount of vapor delivered to the gas as it passes through humidifier 18. This is a function of, among other things, the density of the vapor in chamber 38, which depends in part on the rate at which the reservoir of fluid 40 is evaporated. Based on this relationship, the degree of the increase in the circuit humidity level of the gas passing through humidifier 18 can be controlled via control module 28 by adjusting one or more humidifier parameters that affect the rate of evaporation of the reservoir of fluid 40, such as the temperature of heating element 42, the size of chamber inlet 44, the size of chamber outlet 46, the amount of fluid in reservoir of fluid 40, the surface area of reservoir of fluid 40, the temperature of the reservoir of fluid 40, or other humidifier parameters. The one or more humidity parameters are adjusted by control module 28 via an operative link.

It will be appreciated that humidifier 18 may include any suitable device for delivering vapor to the gas in circuit 12 to elevate the humidity level of the gas in an adjustable manner. For example, U.S. Pat. No. 5,655,542, the contents of which are incorporated herein by reference, teaches a passive humidifier for use with a PAP device that may be implemented as humidifier 18 in one embodiment.

As shown in FIG. 1, humidifier 18 includes a sensor 48 that monitors a humidifier parameter. In the embodiment shown, sensor 48 is associated with heating element 42 and monitors the temperature of heating element 42. However, in other embodiments, sensor 48 may instead be disposed within chamber 38 and used to monitor the temperature of the reservoir of fluid 40. Sensor 48 communicates information associated with the monitored humidifier parameter to control module 28 via an operative link. It will be appreciated that although humidifier 18 is illustrated as being disposed in circuit 12 downstream from pressurizing flow module 16, in other embodiments, humidifier 18 may be disposed in an upstream position from pressurizing flow module 16.

Patient treatment system 10 includes a monitor 50 that is disposed outside of patient circuit 12. Monitor 50 monitors one or more ambient condition parameters of the breathable gas prior to the breathable gas being introduced into the patient circuit at intake 14. For example, the ambient condition parameters monitored by monitor 50 include an ambient humidity level (via, e.g., a relative humidity sensor, a capacitive humidity sensor, a resistive humidity sensor, etc.) and/or an ambient temperature (via, e.g., a thermometer, a thermostat, a thermocouple, a thermistor, etc.). It is to be understood that other ambient condition parameters may be monitored including, for example, a barometric pressure (via, e.g., a piezo-resistive barometric pressure sensor, a mercury barometric pressure sensor, etc.) or other parameters. Monitor 50 is operatively linked to control module 28, and communicates information associated with the ambient condition parameters monitored to control module 28 via the operative link.

Figure 4:
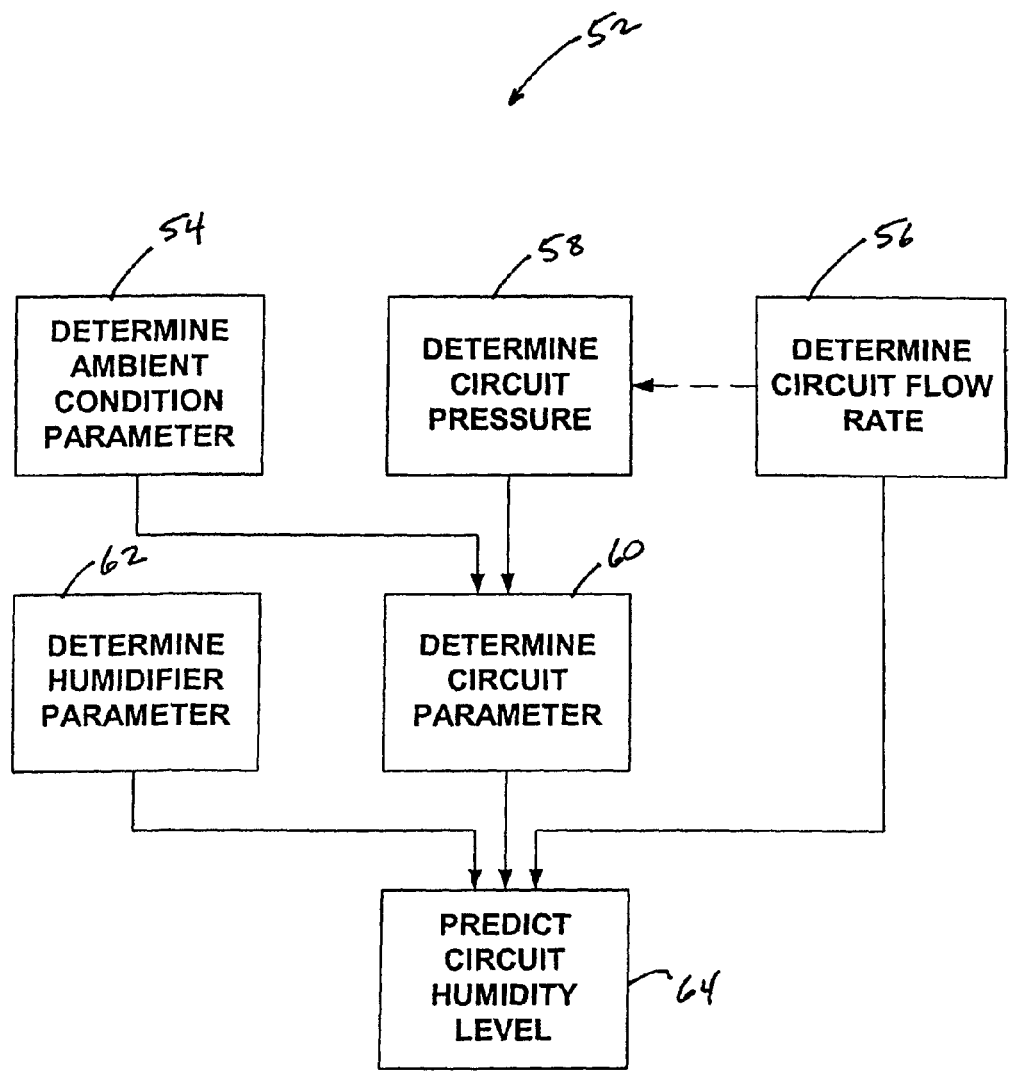
FIG. 4 illustrates a method of predicting a circuit humidity level in accordance with an embodiment of the invention.

FIG. 4 illustrates a method 52 of operation of the present invention. Specifically, the method entails predicting the circuit humidity level. At an operation 54, a determination of one or more ambient condition parameters is made. The ambient condition parameters are determined by control module 28 based on information received by control module 28 from monitor 50. As noted above, the ambient condition parameters may include, for example, the ambient humidity level, the ambient temperature, and/or the ambient barometric pressure. It will be appreciated that humidity level, as used herein, may include monitoring and/or determinations made with respect to any one of absolute humidity level, relative humidity level, or dewpoint.

Method 52 includes an operation 56, at which the circuit flow rate of the gas in circuit 12 is determined by control module 28. In the embodiment of patient treatment system 10 illustrated in FIG. 3, control module 28 determines the circuit flow rate by processing a signal generated by pressure/flow sensor 22. As another example, the circuit flow rate may be determined without monitoring the gas in circuit 12 with a sensor, but rather may be based on one or more control settings, such as a blower speed, a valve control setting, or other control settings.

At an operation 58, the circuit pressure of the gas in circuit 12 is determined by control module 28. In the embodiment of system 10 shown in FIG. 3, the circuit pressure is determined based on, for example, a signal generated by a pressure/flow sensor 22 operatively coupled to patient circuit 12. Alternatively, the circuit pressure may be determined based on one or more control settings, similar to the determination of the circuit flow rate based on control settings as described above, such as the pressure setting to be delivered to the patient.

Method 52 includes an operation 60, at which one or more circuit parameters of the gas in patient circuit 12 are determined by control module 28. In the embodiment shown, the circuit parameters include the circuit temperature and the circuit humidity level upstream from humidifier 18. The parameters of the gas, including the temperature and the humidity level prior to entering humidifier 18, are determined because as pressurizing flow module 16 elevates the flow rate and the pressure of the gas, the temperature and humidity level of the gas are indirectly altered due to the change in pressure. The circuit parameters may be determined based on the determination of the ambient condition parameters made by control module 28 via monitor 50 at operation 54 and the determination(s) of the circuit pressure and/or the circuit flow rate made at operations 56, 58. Alternatively, one or more of the circuit parameters, such as temperature, may be measured directly via one or more sensors disposed within the circuit.

At an operation 62, one or more humidifier parameters are determined by control module 28. The humidifier parameters are related to the increase in the circuit humidity level applied to the gas in circuit 12 as it passes through humidifier 18. In the embodiment illustrated, control module 28 determines the humidifier parameters based on information related to the temperature of heating element 42 provided by sensor 48. The temperature of heating element 42 is associated with the temperature of reservoir of fluid 40 held in chamber 38, which corresponds to the rate of evaporation of the reservoir of fluid 40. In other embodiments, the temperature of heating element 42 may be monitored based on a control setting that controls the temperature of heating element 42. Alternatively, the temperature of the reservoir of fluid 40 may be monitored directly by a temperature sensor (e.g., thermocouple, thermometer, or other temperature sensing device).

Method 52 includes an operation 64, at which the circuit humidity level is predicted by control module 28. This determination is based on a predicted rise in the humidity of the gas as a result of passing through humidifier 18. As has been outlined above, this rise in the humidity level is dependent on circuit flow rate determined at operation 56 the circuit parameters determined at operation 60, and the humidifier parameters determined at operation 62. In one embodiment, the humidity level may be determined based on a look-up table. The values in the look-up table may be derived via an algorithm, or determined experimentally.

Figure 5:
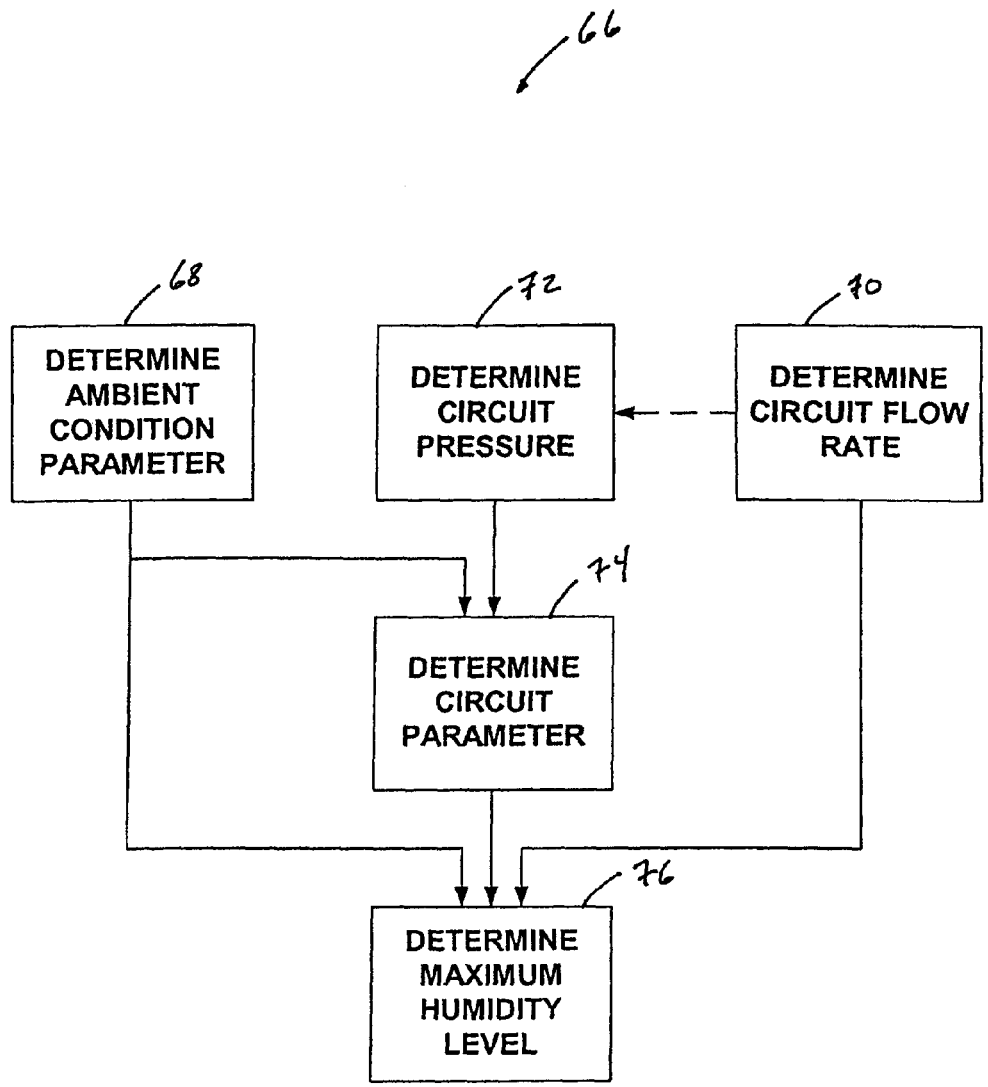
FIG. 5 illustrates a method of determining a maximum humidity level according to an embodiment of the invention.

Referring to FIG. 5, a method 66 of determining a maximum humidity level is illustrated according to an embodiment of the invention. The maximum humidity level is the highest level to which the circuit humidity level can be elevated without forming condensation within circuit 12. Method 66 includes operations 68, 70, 72, and 74, which correspond to operations 54, 56, 58, and 60 of method 52, respectively, and generate determinations of the ambient condition parameters, the circuit flow rate, the circuit pressure, and the circuit parameters by control module 28 according to the manner described above with respect to operations 54, 56, 58, and 60. Thus, details of operations 68, 70, 72, and 74 are omitted for the sake of brevity.

At an operation 76, the maximum humidity level is determined. The determination of the maximum humidity level is based on the circuit flow rate determined at operation 70, the ambient condition parameters determined at operation 68, and the circuit parameters determined at operation 74. In one embodiment, the maximum humidity level may be determined based on a look-up table. The values in the look-up table may be derived via an algorithm, or determined experimentally.

Turning to FIG. 6, an embodiment of a method 78 of operating patient treatment system 10 is illustrated. Method 78 includes an operation 80 at which the system 10 is activated. In an example embodiment, system 10 is activated in response to input received by system 10 via control interface 30, and includes activating pressurizing flow module 16 and humidifier 18. The present invention also contemplates that the patient treatment system can be activated (and deactivated) automatically, for example when the system detects that the patient is breathing into patient interface 17. An example of an auto on/off system is described in U.S. Pat. No. 6,629,527.

Method 78 includes an operation 82, at which a target humidity level is determined. In one embodiment, the target humidity level is automatically set at the maximum humidity level, which is determined by control module 28 at operation 82 according to method 66. In another embodiment, determining the target humidity level may include receiving a selected humidity level input to system 10 at control interface 30. At an operation 84, the current circuit humidity level downstream of humidifier 18 is predicted. For example, in one embodiment, the circuit humidity level is predicted by control module 28 according to method 52. The prediction of the current circuit humidity level is then compared with the target humidity level by control module 28 at an operation 86. This comparison includes determining if the circuit humidity level is substantially equal to the target humidity level. For example, if the circuit humidity level falls within a predetermined range that is determined based on the target humidity level, then the circuit humidity level and the target humidity level may be determined to be substantially equivalent. In one embodiment, the predetermined range includes circuit humidity levels within range boundaries that are offset from the target humidity level by plus and minus a predetermined amount. In another embodiment, the predetermined range may only include circuit humidity levels within range boundaries wherein one of the range boundaries is set at or near the target humidity level and the other range boundary is set either above or below the target humidity level by a predetermined offset.

If the target humidity level and the circuit humidity level are substantially equal, then method 78 returns to operations 82 and 84. However, if the target humidity level and the circuit humidity level are not substantially equal, then the method proceeds to an operation 88. At operation 88, control module 28 adjusts one or more humidifier parameters. In one embodiment, the humidifier parameter that is adjusted is the temperature of heating element 42. The temperature of heating element 42 may be adjusted in the appropriate direction (e.g., hotter or cooler) by a predetermined amount, or the amount of adjustment may be based on the degree of the difference in the values of the target humidity level and the circuit humidity level.

At an operation 90, a determination is made as to whether system 10 is to be deactivated. In an exemplary embodiment, the determination made at operation 90 may include determining if a deactivation command has been input to system 10 at control interface 30. Of course, the present invention also contemplates automatically deactivating the system and/or issuing a deactivation signal if, for example, patient breathing into the patient interface 17 is no longer detected. If no deactivation command has been received by system 10, then method 78 returns to operations 82 and 84. If a deactivation command has been received by system 10, then system 10 is deactivated at an operation 92. Deactivating system 10 includes deactivating pressurizing flow module 16 and humidifier 18. In one embodiment, deactivating system 10 may include deactivating only one or the other of pressurizing flow module 16 and humidifier 18.

In accordance with one aspect of the present invention, the humidity level of the gas in the circuit can be determined without use of a humidity sensor in the circuit. The determined humidity level in the circuit can then be fed back to the processor in a closed loop to enable the patient to set and/or control the humidity level for increased comfort, and optionally without generating excessive condensation in the system.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, the operative links referenced throughout this disclosure may be hardwire, fiber optic, or wireless communication systems, to name some examples. It is to be further understood that the present invention contemplates that, to the extent possible, one or more features of any embodiment can be combined with one or more features of any other embodiment.

What is claimed is:

1. A method of determining humidity of gas delivered to a user, the method comprising:
providing a pressure support system that includes a gas flow generator and a patient circuit operatively coupled to an outlet of the gas flow generator, wherein the patient circuit is adapted to carry a flow of gas from the pressure support system to an airway of a patient;
providing a humidification system that includes a humidification chamber adapted to hold a quantity of fluid, and a heater adapted to heat the fluid in the humidification chamber, wherein the humidification chamber is provided in-line with the patient circuit;
measuring a first humidity level of ambient gas outside the patient circuit;
providing ambient gas into the patient circuit using the gas flow generator;

determining at least one of the pressure or the flow rate within the patient circuit upstream of the humidification chamber;

determining a second humidity level of gas within the patient circuit prior to entering the humidification chamber using at least the first humidity level and one or more of the pressure within the patient circuit upstream of the humidification chamber or the flow rate within the patient circuit upstream of the humidification chamber;

causing a gas flow from the gas flow generator to pass through at least a portion of the humidification chamber so as to add vapor to the flow in the patient circuit;

determining a rate at which the vapor is added to the gas drawn into the patient circuit; and determining a third humidity level of the gas in the patient circuit downstream from the humidifier based on (a) the second humidity level, (b) one or more of the pressure within the patient circuit upstream of the humidification chamber or the flow rate within the patient circuit upstream of the humidification chamber, and (c) a rate at which the vapor is added to the gas drawn into the patient circuit.

2. The method of claim 1, wherein the rate at which the vapor is added to the gas drawn into the patient circuit is determined based on one or more of a temperature of the heater, a temperature of the fluid within the humidifier chamber, or the flow rate within the patient circuit upstream of the humidifier.

3. The method of claim 1, further comprising adjusting the rate at which the vapor is added to the gas drawn into the patient circuit based upon the determination of the third humidity level in a feedback manner.

4. A patient treatment system comprising:
a patient circuit adapted to carry a flow of gas from a gas source to a patient;
a pressuring flow module operatively coupled to an inlet of the patient circuit that generates the flow of gas within the patient circuit;
a humidifier disposed in line with the patient circuit that elevates a humidity of the flow of gas in the patient circuit to a circuit humidity level, wherein the humidifier comprises a reservoir of water and a heating element that heats the reservoir of water;
a monitor adapted to monitor a humidifier parameter that includes one or more of a temperature of the reservoir of fluid, or a temperature of the heating element;
a humidity sensor adapted to determine an ambient humidity of gas outside the patient circuit; and
a processor that determines:
at least one of the pressure or the flow rate within the patient circuit upstream of the humidifier,
a humidity level of the gas in the patient circuit upstream of the humidifier based on at least the ambient humidity and one or more of the pressure within the patient circuit upstream of the humidifier or the flow rate within the patient circuit upstream of the humidifier, and
a humidity level of the gas in the patient circuit downstream from the humidifier based on the humidity level of the gas in the patient circuit upstream of the humidifier, one or more of the pressure within the patient circuit upstream of the humidifier or the flow rate within the patient circuit upstream of the humidifier, and the humidifier parameter.

5. The system of claim 4, further comprising an interface, wherein the flow rate within the patient circuit upstream of the humidifier, the pressure within the patient circuit upstream of the humidifier, or the a humidity level of the gas in the patient circuit downstream from the humidifier is selectably controlled via the interface.

6. The system of claim 4, wherein the monitor is a temperature sensor that detects one or more of the temperature of the heating element or a control setting of the humidifier.

7. The system of claim 4, further comprising a flow sensor and a pressure sensor, and wherein the processor determines the pressure within the patient circuit upstream of the humidifier based at least in part on an output of the pressure sensor and determines the flow rate within the patient circuit upstream of the humidifier based at least in part on an output of the flow sensor.

8. The system of claim 7, wherein the processor determines a maximum humidity level to which the humidity level of the gas in the patient circuit can be elevated without forming condensation within the patient circuit, the determination of the maximum humidity level being based on the flow rate of the gas in the patient circuit upstream of the humidifier, the pressure within the patient circuit upstream of the humidifier, and at least one of the temperature of the reservoir of water and the temperature of the heating element.

9. The system of claim 8, wherein the determination of the humidity level of the gas in the patient circuit downstream from the humidifier is implemented in a feedback loop to automatically control the heating element such that the humidity level of the gas in the patient circuit downstream from the humidifier is maintained substantially equal to the maximum humidity level.

10. A method of determining humidity of gas within a patient circuit, the method comprising:
providing a pressure support system that includes a gas flow generator and a patient circuit operatively coupled to an outlet of the gas flow generator, and wherein the patient circuit is adapted to carry a flow of gas from the pressure support system to an airway of a patient;
providing a humidification system that includes a humidification chamber adapted to hold a quantity of liquid, and a heater adapted to heat the liquid in the humidification chamber, wherein the humidification chamber is provided in-line with the patient circuit;
determining a first humidity level of ambient gas outside the patient circuit;
drawing ambient gas into the patient circuit;
pressurizing the gas drawn into the patient circuit using the gas flow generator;
determining at least one circuit parameter of the gas within the patient circuit upstream of the humidification system using at least the first humidity level and one or more of the pressure within the patient circuit upstream of the humidification system or the flow rate within the patient circuit upstream of the humidification system;
causing a gas flow from the gas flow generator to pass through at least a portion of the humidification chamber so as to add humidity to the gas flow in the patient circuit; and
determining a second humidity level of the gas within the patient circuit after the humidity has been added thereto based on (a) the at least one circuit parameter and (b) the first humidity level.

11. The method of claim 10, wherein the at least one circuit parameter of the gas comprises one or more of a temperature of the gas in the patient circuit upstream of the humidification system or a humidity of the gas in the patient circuit upstream of the humidification system.

12. The method of claim 10, wherein the second humidity level is also determined based on (c) a rate at which vapor is added to the gas.

13. The method of claim 12, wherein the rate is estimated based on one or more of a temperature of the heater or a temperature of a the liquid.

14. A method of delivering gas to a patient, the method comprising:

providing a pressure support system that includes a gas flow generator and a patient circuit operatively coupled to an outlet of the gas flow generator, and wherein the patient circuit is adapted to carry a flow of gas from the pressure support system to an airway of a patient;

providing a humidification system that includes a humidification chamber adapted to hold a quantity of liquid, and a heater adapted to heat the liquid in the humidification chamber, wherein the humidification chamber is provided in-line with the patient circuit;

determining a first humidity level of the gas prior to entering the patient circuit;

determining the pressure of the gas within the patient circuit;

determining a rate of flow of the gas within the patient circuit;

determining a second humidity level of the gas within the patient circuit prior to entering the humidification chamber using at least the first humidity level and one or more of the pressure of the gas within the patient circuit or the rate of flow of the gas within the patient circuit;

determining at least one parameter of the operation of the heater; and determining a third humidity level of the gas in the patient circuit downstream from the humidifier based at least in part on the flow rate of the gas within the patient circuit, the pressure of the gas within the patient circuit, the second humidity level, and the at least one parameter of the operation of the heater.

15. The method of claim 14, wherein the at least one parameter of the operation of the heater comprises one or more of a temperature of the heater or a temperature of the liquid.

16. The method of claim 14, further comprising determining a maximum humidity level to which the third humidity level of the gas within the patient circuit can be elevated without forming condensation within the patient circuit based on one or more of (a) the rate of flow of the gas within the patient circuit, (b) the pressure of gas within the patient circuit, (c) the at least one parameter of the operation of the heater, or (d) the first humidity level.

17. The method of claim 16, further comprising implementing the third humidity level in a feedback loop to automatically control the at least one parameter of the operation of the heater such that the third humidity level is maintained substantially equal to the maximum humidity level.

18. The method of claim 17, further comprising:

receiving a selected humidity level; and implementing the third humidity level of the gas in the patient circuit downstream from the humidifier in a feedback loop to automatically control the at least one parameter of the operation of the heater such that the third humidity level is maintained substantially equal to the selected humidity level.

* * * * *